US010661042B2

(12) United States Patent
Heesch

(10) Patent No.: US 10,661,042 B2
(45) Date of Patent: May 26, 2020

(54) BREATHING AIR SUPPLY WITH REBREATHING SYSTEM

(71) Applicant: Drägerwerk AG & Co. KGaA, Lübeck (DE)

(72) Inventor: Ralf Heesch, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 386 days.

(21) Appl. No.: 15/531,853

(22) PCT Filed: Nov. 17, 2015

(86) PCT No.: PCT/EP2015/002293
§ 371 (c)(1),
(2) Date: May 31, 2017

(87) PCT Pub. No.: WO2016/087020
PCT Pub. Date: Jun. 9, 2016

(65) Prior Publication Data
US 2017/0266407 A1  Sep. 21, 2017

(30) Foreign Application Priority Data

Dec. 1, 2014 (DE) .................. 10 2014 017 712

(51) Int. Cl.
*A61M 16/10* (2006.01)
*A61M 16/08* (2006.01)
(Continued)

(52) U.S. Cl.
CPC .... *A61M 16/1045* (2013.01); *A61M 16/0045* (2013.01); *A61M 16/01* (2013.01);
(Continued)

(58) Field of Classification Search
CPC ............ A61M 16/1045; A61M 16/105; A61M 16/1075; A61M 16/0045; A61M 16/01;
(Continued)

(56) References Cited

U.S. PATENT DOCUMENTS 4,108,172 A * 8/1978 Moore, Jr. ............ A61M 16/22
128/205.12
4,303,601 A * 12/1981 Grimm ............. A61M 16/1075
261/142
(Continued)

FOREIGN PATENT DOCUMENTS

CN 1958087 B 1/2011
CN 102210911 A 10/2011
(Continued)

OTHER PUBLICATIONS

Wydeven, Theodore. A survey of some regenerative physico-chemical life support technology. National Aeronautics and Space Administration, Ames Research Center, 1988.

*Primary Examiner* — Bradley H Philips
*Assistant Examiner* — Vincent D Hoang
(74) *Attorney, Agent, or Firm* — McGlew and Tuttle, P.C.

(57) ABSTRACT

An apparatus for supplying breathing air to a person includes a rebreathing system arranged in the air supply circuit, which removes $CO_2$ at least in part present in the person's expiration air with a $CO_2$ absorber, and treats the expiration air to supply treated air to the person again as inhalation air. The apparatus includes a condensate collection container (9) collecting water forming in the air supply circuit. The condensate collection container (9) is arranged at least in part below a reaction zone (17) of the $CO_2$ absorber (1). At least one heat exchanger (10, 14) is provided in the $CO_2$ absorber, via which heat from the air, which flows through the $CO_2$ absorber and is heated as a result of the
(Continued)

exothermic $CO_2$ absorption reaction occurring in the reaction zone of the $CO_2$ absorber, is dissipated.

23 Claims, 1 Drawing Sheet

(51) Int. Cl.
*A61M 16/22* (2006.01)
*A61M 16/00* (2006.01)
*A61M 16/01* (2006.01)

(52) U.S. Cl.
CPC .... *A61M 16/0808* (2013.01); *A61M 16/1005* (2014.02); *A61M 16/22* (2013.01); *A61M 2016/0027* (2013.01); *A61M 2016/0033* (2013.01)

(58) Field of Classification Search
CPC .. A61M 16/0808; A61M 16/12; A61M 16/22; A61M 16/009; A61M 16/0093; A61M 16/10; A61M 16/106; A61M 16/1065; A61M 16/107; A61M 16/1095; A61M 2016/0027; A61M 2202/0225; A61M 2205/366; A62B 19/00
USPC ....................... 96/110; 165/231, 104.24, 185
See application file for complete search history.

(56) References Cited

U.S. PATENT DOCUMENTS

| | | | |
|---|---|---|---|
| 4,502,876 A * | 3/1985 | Behnke, Jr. | A62B 19/00 55/516 |
| 5,487,380 A * | 1/1996 | Grabenkort | A61M 16/22 128/204.15 |
| 6,523,538 B1 * | 2/2003 | Wikefeldt | A61M 16/01 128/204.18 |
| 7,591,267 B2 | 9/2009 | Mashak et al. | |
| 8,596,272 B2 | 12/2013 | Koulechov et al. | |
| 8,696,802 B2 * | 4/2014 | O'Coin | B01D 53/0438 165/10 |
| 2002/0148471 A1 | 10/2002 | Hirabayashi | |
| 2007/0051367 A1 | 3/2007 | Mashak et al. | |
| 2010/0199993 A1 * | 8/2010 | Koulechov | A61M 16/0808 128/205.28 |
| 2011/0247618 A1 * | 10/2011 | Koch | A62B 7/00 128/204.15 |

FOREIGN PATENT DOCUMENTS

| | | |
|---|---|---|
| CN | 104159641 A | 11/2014 |
| DE | 100 47 137 A1 | 4/2002 |
| DE | 694 29 817 T2 | 8/2002 |
| DE | 102 10 292 A1 | 10/2002 |
| DE | 10 2006 040 886 A1 | 4/2007 |
| DE | 10 2009 007 980 A1 | 12/2010 |
| EP | 2 374 509 A1 | 10/2011 |
| WO | 99/33523 A1 | 7/1999 |

* cited by examiner

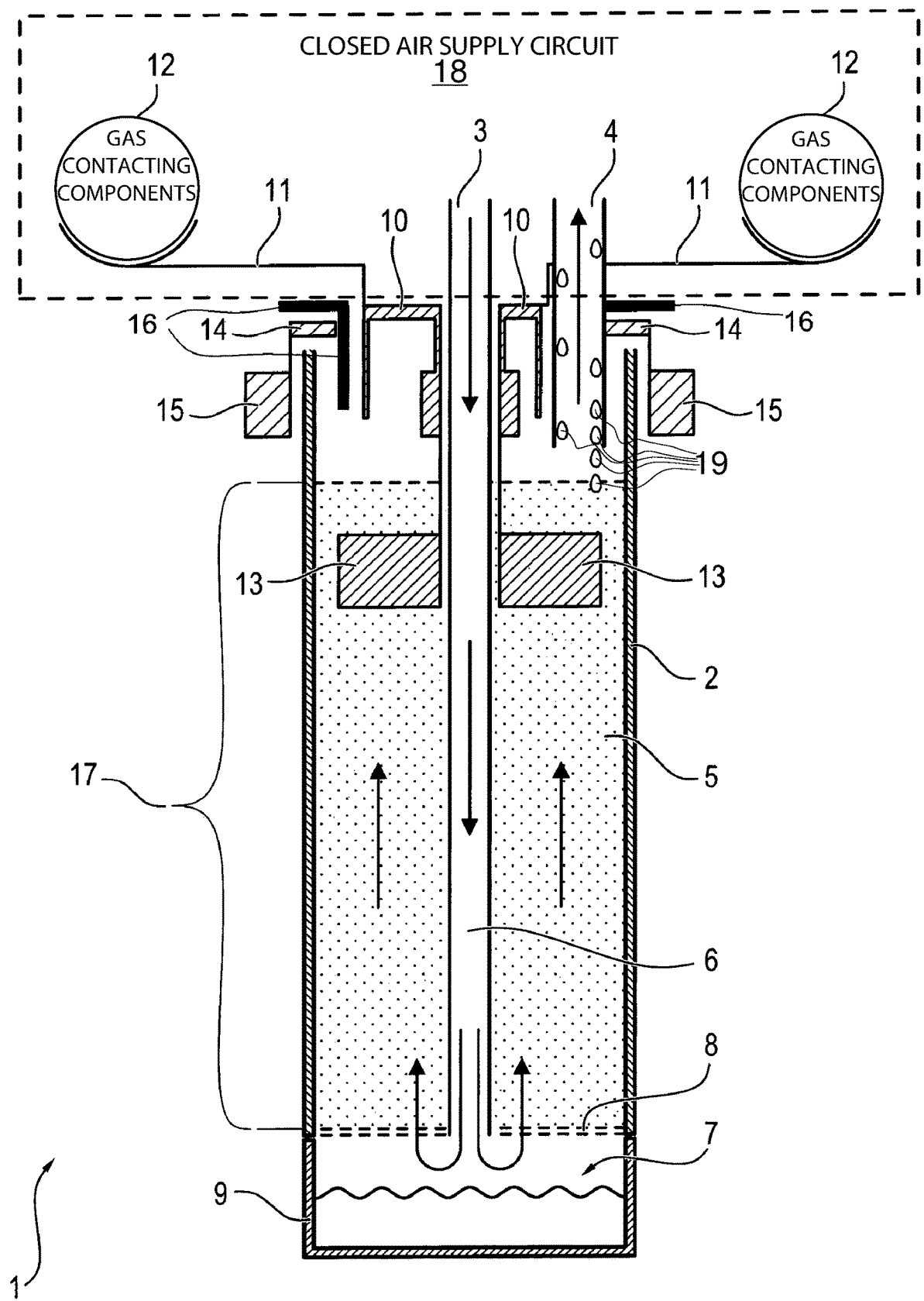

BREATHING AIR SUPPLY WITH REBREATHING SYSTEM

CROSS REFERENCE TO RELATED APPLICATIONS

This application is a United States National Phase Application of International Application PCT/EP2015/002293 filed Nov. 17, 2015, and claims the benefit of priority under 35 U.S.C. § 119 of German Application 10 2014 017 712.2 filed Dec. 1, 2014, the entire contents of which are incorporated herein by reference.

FIELD OF THE INVENTION

The present invention pertains to a device for breathing air supply for a person with a rebreathing system, which is arranged in the closed air supply circuit and which at least partly removes $CO_2$ present in the air exhaled by the person by means of a $CO_2$ absorber and processes the air, especially enriches it with oxygen, such that the air thus processed can again be fed as air to be inhaled to the person.

BACKGROUND OF THE INVENTION

Devices for breathing air supply for a person with rebreathing system are used in both stationary devices, e.g., anesthesia or ventilation systems, as well as in so-called closed-circuit breathing systems, which are used for rescue operations and for diving. An essential feature of these breathing air supply systems is that the breathing air for supplying a person, especially a patient or a rescue person is circulated in a closed circuit. Part of the $CO_2$ contained in the air exhaled by the person must first be removed from that air within this closed circuit. Furthermore, oxygen is often fed to the air and the temperature of the air is controlled as needed.

If corresponding systems are used for anesthesia devices, $CO_2$ is first removed from the breathing gas exhaled by the patient and the breathing gas is then enriched with oxygen and volatile anesthetic. The utilization of oxygen and volatile anesthetic gases is considerably improved in such a closed process and both the costs are reduced and the environment is protected.

In the prior-art closed-circuit breathing systems with rebreathing system, $CO_2$ is extracted from the breathing gas, as a rule, with so-called breathing lime. Both heat and moisture are generated during the absorption of $CO_2$, because an exothermic reaction is involved here. It is problematic in this connection that the moisture generated during the $CO_2$ absorption may condense on the breathing system components arranged downstream, especially on sensors or valves and thus may lead to impairment of the function or even failures.

To avoid corresponding impairments, electrical or actively regulated heating systems are known, e.g., in the area of anesthesia devices, and these systems prevent the generation of moisture in the breathing system or at least ensure that a corresponding condensation will occur at locations specially intended for this purpose. Such systems often have a comparatively complicated regulation technology, are expensive and have an increased energy consumption.

A carbon dioxide absorber for a closed-circuit breathing system, which has a gas inlet and a gas outlet on the upper side and a condensate collection tank in the lower area, is known from DE 10 2009 007 980 A1. A bed of granular breathing lime, which binds carbon dioxide from a patient during the operation, is located on a perforated plate in the absorber housing. The exhaled gas enters a collection space below the perforated plate via the gas inlet and a duct arranged centrally in the absorber housing and flows from there via the perforated plate and the breathing lime to the gas outlet. Further, a condensate collection tank with a layer of a water-binding substance in the form of a superabsorbing polymer, which substance collects and stores the condensate generated, is located in the lower area of the collection space. The substance thus prevents condensate from flowing back into the breathing lime.

An alternative technical solution for removing moisture from the exhaled air in the closed ventilation circuit, which is based on the use of a room-temperature heat exchanger, is known from DE 10 2006 040 886 A1. A heat exchanger is provided in the closed ventilation circuit for removing water vapor from the ventilation gases to prevent condensation within the closed ventilation circuit. The heat exchanger is arranged in this case downstream of a $CO_2$ absorber and receives the ventilation gases from the $CO_2$ absorber before they flow to the inhalation branch of the closed ventilation circuit. The heat exchanger contains a number of inflow tubes and outflow tubes, which are each open towards a sump, which is detachably fastened to the heat exchanger. The condensate, which condenses from the ventilation gases within the heat exchanger, collects in the sump.

It is common to the prior-art closed-circuit breathing systems that the generation of moisture is not regularly reduced, but the condensation is specifically deflected in the most favorable case into a certain area, which must be maintained and monitored by the user as a consequence of this technical solution.

SUMMARY OF THE INVENTION

Based on the prior-art devices for supplying a person with breathing air, which have a rebreathing system, a basic object of the present invention is to improve these systems such that moisture will be captured and collected where it is generated and transportation of moisture into the closed ventilation circuit is reliably prevented from occurring. It is desirable in this connection that moisture collect at a location that is a maintenance point for the user anyway. The condensate being formed based on the exothermic reaction in the $CO_2$ absorber shall preferably collect in the area of the $CO_2$ absorber, because this absorber, containing the breathing lime, does require regular maintenance anyway. Since the breathing lime is consumed after a certain time, it must be replaced. Another essential part of the object is to remove the heat generated during the exothermic reaction in the carbon dioxide absorber from the reaction zone in a suitable manner.

A device for supplying a person with breathing air with a rebreathing system, which is arranged in the closed air supply circuit and which at least partly removes $CO_2$ present in the air exhaled by the person by means of a $CO_2$ absorber and processes the exhaled air such that the processed air can again be fed as air to be inhaled to the person, and with a condensate collection tank, in which water formed in the closed air supply circuit can be collected, was improved according to the present invention such that the condensate collection tank is arranged at least partly under a reaction zone of the $CO_2$ absorber and that at least one heat exchanger is provided in the $CO_2$, and heat is removed by said heat exchanger from the air which flows through the $CO_2$ absorber and is being heated based on the exothermic $CO_2$ absorption reaction taking place in the reaction zone of the $CO_2$ absorber. It is conceivable, in principle, in this connection to provide one heat exchanger or a plurality of heat exchangers, which are at least partly indirectly or directly in contact with the reaction zone and/or which are arranged in an area that is located fluidically downstream of the reaction zone. The technical solution according to the present invention is thus characterized in that the moisture formed within the reaction zone of the $CO_2$ absorber is drawn off directly into a condensate collection tank located under the reaction zone in the housing of the $CO_2$ absorber and the heat being formed within the reaction zone based on the exothermic reaction is at the same time removed. It is ensured by these measures, in particular, that drier and cooler air will leave the $CO_2$ absorber.

According to a first special embodiment of the present invention, the heat exchanger is configured in the form of a heat-conducting plate. The heat-conducting plate is arranged either above the lime provided in the $CO_2$, preferably as a bed of lime, or else at least partly within the lime. Such a heat-conducting plate is preferably arranged at right angles to the gas flow direction and has suitable perforations, through which the breathing gas can flow. Such a heat-conducting element may be configured, for example, in the form of a perforated plate made of a material having good thermal conductivity. According to a special embodiment of the present invention, heating lugs, which project from the heat-conducting element and protrude into the reaction zone, especially into the bed of breathing lime, are provided at the heat-conducting element, especially the heat-conducting plate. It is possible in this manner to achieve heat dissipation within the reaction zone over a large surface. The circumstance that, depending on the saturation of the lime with carbon dioxide, the reaction zone and hence the area in which moisture and heat are predominantly produced based on the exothermic reaction, is displaced in the flow direction, i.e., farther upward in case of flowthrough from bottom to top as the operating time of the $CO_2$ increases, is advantageously taken into account in dimensioning and configuring the heating lugs. Starting from the areas of the lime, especially, a bed of lime, which is first reached by the flow, the reaction zone is therefore displaced with increasing operating time into the areas which are reached by the flow later and are located farther back in the flow direction.

In addition to a first heat exchanger, which is arranged behind or at least in some areas within the breathing lime and is preferably configured in the form of a heat-conducting element, it is conceivable to provide an additional heat exchanger, which is arranged within the $CO_2$ absorber downstream of the first heat exchanger in the flow direction of the breathing air. A further cooling of the breathing gas takes place in this case after this gas has already flown through and past the first heat exchanger and before the breathing gas has left the $CO_2$ absorber, especially the housing of the absorber.

According to a special variant of the present invention, at least one element for heat insulation is provided, which insulates the first heat exchanger and/or the heat-conducting elements against the area surrounding them and against adjacent components. In particular, the first heat exchanger has, in at least some areas, a heat insulation, which is preferably made of a suitable plastic material. Such a heat insulation is meaningful above all in cases in which an additional heat exchanger arranged downstream of the first heat exchanger is provided in addition to the first heat exchanger. Since the first heat exchanger has, in a suitable manner, a heat-conducting plate, which is arranged at least in the vicinity of the additional heat exchanger, heat insulation is meaningful in this area, especially between the first and second heat exchangers. If a heat insulation at the same time defines a flow duct, through which the breathing gas flows, it is, furthermore, meaningful if the heat insulation is configured at the same time such that gas-tightness is guaranteed. This can preferably be achieved, in turn, by the use of a plastic, especially an elastomer, e.g., silicone, TPE or EPDM.

In a special embodiment, the housing of the $CO_2$ absorber is manufactured, in at least some sections, of an at least translucent or transparent plastic. This has the advantage that a change in the color of the lime, which occurs when the lime is depleted or at times also when it has dried out and is thus no longer able to assume its function, is visible. This change in color is an important signal for the user of a device, showing that the breathing line must be replaced. In a special embodiment, the condensate tank is in direct contact with a tank in which the breathing lime is located, so that the condensate tank is removed at the same time when the breathing lime cartridge is removed. It is, of course, also conceivable to configure the condensate collection tank as a separate component, which is emptied as soon as the breathing lime cartridge must be replaced. It is advantageous in any case if the condensate collection tank is dimensioned such that it must be emptied at the earliest when the breathing lime within the $CO_2$ absorber has also been consumed. A special absorbent material, which absorbs the condensed moisture from the breathing gas, may advantageously be provided for this within the condensate collection tank.

Heat removed from the $CO_2$ absorber is advantageously utilized within the closed ventilation circuit in order to heat, for example, sensors and/or valves in a specific manner. The heat, which is generated anyway, can be utilized in this manner in order to reliably prevent moisture from condensing on the above-described components. The heat removed by the first and/or additional heat exchanger provided according to the present invention is especially preferably used for a flow sensor and/or a pressure sensor within the closed breathing circuit. In addition to the reduction of the percentage of $CO_2$ in the breathing gas, an additional processing of the breathing air is carried out in the closed-circuit breathing system with rebreathing, and oxygen, at least one anesthetic and/or analgesic are added to the breathing gas. The device configured according to the present invention is thus especially suitable for use in connection with anesthesia devices, respirators and/or closed-circuit respirators for diving or for rescue operations.

It is always essential for the present invention that the heat generated within the carbon dioxide absorber in the corresponding systems be removed and preferably used for additional components within the closed-circuit breathing system. The cooling of the breathing air is carried out here within the $CO_2$ absorber such that the moisture formed in the process remains within the $CO_2$ absorber housing and enters a condensate collection tank or condensate collection area of the $CO_2$ absorber housing, which tank or area is specially intended for this purpose.

The present invention will be explained below without limitation of the general inventive idea with reference to the figures based on exemplary embodiments. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1 is a sectional view of a carbon dioxide absorber configured according to the present invention with a bed of breathing lime.

DESCRIPTION OF THE PREFERRED EMBODIMENTS

Referring to the drawings, FIG. 1 shows an absorber unit 1 configured according to the present invention for absorbing carbon dioxide ($CO_2$), as it can be used in a suitable manner in a closed air supply circuit 18 of closed-circuit breathing apparatuses with rebreathing system. The housing 2 of the absorber unit 1 has a gas inlet 3, via which the breathing gas exhaled by the person is fed to the absorber 1. Further, a gas outlet 4 is provided, through which the breathing gas, from which carbon dioxide was extracted, leaves the absorber 1.

A bed of breathing lime 5, through which breathing gas exhaled by the person is sent in order to remove carbon dioxide from it at least partly, is located on a perforated plate 8. The exhaled breathing gas enters a collection space 7 under the perforated plate 8 via a duct 6 arranged centrally in the absorber housing 2 and finally reaches from there the gas outlet 4 via the perforated plate 8 and the breathing lime 5.

A condensate collection tank 9 is provided in the lower area of the collection space 7 of the absorber unit 1, i.e., likewise under the perforated plate 8 with the bed of breathing lime 5 mounted on it, in which the respective $CO_2$ reaction zone 17 is located. The condensate generates in the absorber 9 or the moisture being formed collects in this condensate collection tank 9. The condensate is formed, on the one hand, within the absorber unit 1 based on the reaction taking place in the breathing lime 5, in which water is released, and, on the other hand, based on the specific cooling of the breathing air, which leads directly to an increase in the relative humidity of the air. The breathing gas exhaled by the person thus flows through the breathing lime 5 arranged in the absorber unit 1 from bottom to top, and the breathing gas, from which $CO_2$ had been removed, finally flows back again into the breathing system via the gas outlet 4.

A granular mixture of calcium hydroxide ($Ca(OH)_2$) and sodium hydroxide (NaOH) is used as the breathing lime 5. The following chemical reactions take place while the breathing gas exhaled by the person flows through the bed of breathing lime 5 of the absorber unit 1:

$$CO_2 + H_2O \leftrightarrow H_2CO_3$$

$$H_2CO_3 + 2NaOH \leftrightarrow Na_2CO_3 + 2H_2O$$

$$Na_2CO_3 + Ca(OH)_2 \leftrightarrow CaCO_3 + 2NaOH.$$

Heat and water are generated based on the reactions taking place in the reaction zone 17. Breathing limes 5 of an average configuration are able to absorb 10-15 L of $CO_2$ per 100 g of bulk material. Furthermore, a pH indicator, which changes its color from white to violet at a low pH value and thus indicates that the breathing lime 5 has been consumed, is added to the breathing lime 5.

If the breathing lime 5 has not yet been consumed, the $CO_2$ in the exhaled breathing gas reacts already directly at the point of entry in the lime 5, so that this area initially forms the reaction zone 17. Both heat and moisture are generated during the reaction or the absorption of $CO_2$ based on the exothermic reaction taking place here. The reaction zone 17 migrates farther upward with increasing consumption of lime 5 within the $CO_2$ absorber. The farther the reaction zone 17 has migrated upward, the zone in which moisture is formed is also moving in the direction of the gas outlet 4 of the $CO_2$ absorber unit 1 and hence in the direction of the closed breathing circuit. There is basically a risk in this connection that warm and humid air will enter the closed breathing circuit, in which it will then condense and may be responsible, especially in case of condensation in the area of functional elements, such as valves or pressure and flow sensors, for the failure of these components.

To reliably avoid this effect, a heat exchanger 10, which absorbs the heat being formed in the reaction zone 17, which heat is then removed from the reaction zone 17, especially also from the $CO_2$ absorber housing 2, is provided within the housing 2 of the $CO_2$ absorber unit 1. The heat thus removed is passed on by means of suitable heat-conducting elements 11 to relevant components 12, which are in contact with the breathing gas in at least some areas, especially to pressure and flow sensors within the closed-circuit breathing system. A specific temperature rise takes place in the area of these components 12, so that condensation phenomena are avoided in this area. The corresponding components 12 maintain in this manner a temperature level that is above the ambient temperature, and a tendency towards condensation is thus reduced.

The higher the reaction zone 17 migrates within the bed of breathing lime 5 in the course of the consumption of the breathing lime, the more heat is absorbed by the heat exchanger 10 configured in the form of a heat-conducting plate. To further improve the dissipation of heat from the reaction zone 17, special heat-conducting lugs 13, which are in thermal contact with the heat exchanger 10, are provided within the bed of breathing lime 5. Such heat-conducting lugs 13 may generally be arranged both within the bed of breathing lime 5 and in an area arranged downstream of the bed 5 in the absorber housing 2.

According to the exemplary embodiment shown in FIG. 1, there is an additional measure for avoiding condensation cooling of the purified breathing gas leaving the bed 5. The purified gas flow is sent here through an additional heat exchanger 14, which is cooled by ambient air and hence to room temperature. A corresponding additional temperature exchange may likewise be supported by suitably provided cooling elements 15 or also by a deflected cooling air flow. It is conceivable in this connection that such a cooling air flow is blown out in the direction of the $CO_2$ absorber unit 1 or is drawn off from that unit by means of a fan unit of a connected anesthesia, ventilation or closed-circuit breathing apparatus.

If, as is shown in FIG. 1, two heat exchangers 10, 14 are provided within the carbon dioxide absorber 1, these are heat-insulated from one another by means of a heat insulation 16. Such a heat insulation 16 may be facilitated, for example, by applying a plastic layer, especially an elastomer.

Based on the additional cooling of the breathing gas, brought about by the second heat exchanger 14, condensate 19 is also formed, at least at times, in the area of this heat exchanger 14, and this condensate 19 must be drawn off into the area of the condensate collection tank 9. The condensate 19 now flows through the lime in counterflow to the breathing gas and finally enters the condensate collection tank 9 in the lower area of the $CO_2$ absorber housing 2. Since the condensate 19 flowing in from the second heat exchanger 14 in the direction of the condensate collection tank 9 must pass through the first heat exchanger 10, it is deflected such that it does not flow directly along the first heat exchanger 10 in order thus to avoid an undesired cooling. In particular, the heat-conducting lugs 13 thermally connected to the first heat exchanger 10 are not arranged beneath the surfaces of the second heat exchanger 14, at which condensate 19 is formed and from which it will finally flow off.

The condensate is also disposed of automatically at the time of the cyclical replacement of the lime in the condensate collection tank 9 or condensate reservoir. The filling volume of the condensate collection tank 9 is preferably dimensioned for this reason such that it will not overflow within a usual replacement cycle. The filling level of the condensate collection tank 9 is visible from the outside, so that the user can detect an overfilling in time and respond correspondingly.

To facilitate the optical checking of the bed of breathing lime 5, the $CO_2$ absorber housing 2 is manufactured in at least some sections from a translucent or transparent plastic. It is ensured in this manner that the user can reliably detect a change in the color of the lime 5. A change in the color of the lime 5 takes place as soon as this is depleted or at times also as soon as it has dried out. A change in color thus takes place in cases in which the breathing lime 5 is no longer able to assume its proper function. The change in color thus represents an important signal for the user, so that he can reliably detect that the breathing lime must be replaced.

The corresponding absorber unit 1, especially its bed of breathing lime 5, is configured such that a maximum upper lime filling level is not exceeded, so that the upper maximum filling mark always remains detectable for the user. The second heat exchanger 14 within the $CO_2$ absorber housing 2 is arranged above the bed of breathing lime 5, so that the view to the breathing lime 5 is not made difficult for the user. Both the first heat exchanger 10 in the form of a heat-conducting plate and the second heat exchanger 14, which is cooled by room air, are manufactured from aluminum, copper, brass or a heat-conducing plastic. If the two heat exchangers 10, 14 are in the immediate vicinity of one another, a heat insulation, which preferably also has a gas-tight configuration, is provided between these. This heat insulation may, in turn, contain a plastic or elastomer material, especially silicone, TPE or EPDM. It is advantageous for the manufacture of such a heat exchanger to manufacture this by means of a die-based two-component injection molding method from a combination of heat-conductive plastics and insulating and sealing elastomers.

The technical solution according to the present invention, which is based on the fact that the cooling and the condensation of moisture are brought about specifically at one location, is characterized by a simple configuration and nevertheless guarantees a high level of safety against failure. It is especially advantageous in this connection that the moisture precipitates in an area in which a maintenance point of a breathing air supply system is located anyway. It is essential in this connection that a user be accustomed anyway to check this area visually and to change the lime cartridge at regular intervals. An even greater safety can be achieved by the coupling with an active electric heater in terms of avoiding condensation in systems for supplying persons, especially patients or rescue persons, with breathing air.

While specific embodiments of the invention have been shown and described in detail to illustrate the application of the principles of the invention, it will be understood that the invention may be embodied otherwise without departing from such principles.

The invention claimed is:

1. A device for a breathing air supply for a person with a rebreathing system arranged in a closed air supply circuit, which removes $CO_2$ contained in the exhaled air of the person at least partly, the device comprising:
   a $CO_2$ absorber configured to process the air to be inhaled such that the processed air can again be fed as air to be inhaled to the person;
   a condensate collection tank configured to collect water being formed in the closed air supply circuit, wherein the condensate collection tank is arranged at least partly under a reaction zone of the $CO_2$ absorber; and
   at least one heat exchanger provided in the $CO_2$ absorber, the at least one heat exchanger configured to remove heat from the air, which flows through the $CO_2$ absorber and which is heated based on the exothermic $CO_2$ absorption reaction taking place in the reaction zone of the $CO_2$ absorber;
   at least one functional component; and
   a heat-conducting element, wherein the heat removed from the air by the at least one heat exchanger is sent via the heat-conducting element to the at least one functional component, which is arranged within the closed air supply circuit.

2. A device in accordance with claim 1, wherein the at least one heat exchanger is arranged, with respect to a flow direction of the air, behind the reaction zone in the $CO_2$ absorber.

3. A device in accordance with claim 1, wherein the at least one heat exchanger is arranged within the reaction zone.

4. A device in accordance with claim 1, wherein the at least one heat exchanger is configured as a plate-shaped heat-conducting element.

5. A device in accordance with claim 1, wherein the at least one heat exchanger has, in at least some sections, a plastic-containing heat insulation on an outer surface thereof.

6. A device in accordance with claim 1, wherein the at least one heat exchanger has at least one heat-conducting lug extending into the reaction zone.

7. A device in accordance with claim 1, wherein the at least one heat exchanger can be cooled with ambient air.

8. A device in accordance with claim 1, wherein the at least one functional component is configured as a flow sensor or as a pressure sensor or as both a flow sensor and as a pressure sensor.

9. A device in accordance with claim 1, further comprising at least one material, which binds water, arranged in the condensate collection tank.

10. A device in accordance with claim 1, wherein oxygen or an anesthetic gas is added to the air during the processing or both oxygen and an anesthetic gas are added to the air during the processing.

11. A method supplying breathing air, to a person, with a rebreathing system having a closed air supply circuit, the method comprising the steps of:
   connecting a device comprising: a $CO_2$ absorber; a condensate collection tank; and at least one heat exchanger to the rebreathing system;

processing the air to be inhaled with the $CO_2$ absorber such that the processed air can again be fed as air to be inhaled to the person;

arranging the condensate collection tank at least partly under a reaction zone of the $CO_2$ absorber;

collecting water being formed in the closed air supply circuit in the condensate collection tank;

providing the at least one heat exchanger in the $CO_2$ absorber;

removing heat, with the at least one heat exchanger, from the air which flows through the $CO_2$ absorber and which is heated based on the exothermic $CO_2$ absorption reaction taking place in the reaction zone of the $CO_2$; and providing the rebreathing system in an anesthesia device with the closed air supply circuit, or in a ventilator with the closed air supply circuit or in a a closed-circuit breathing system diving apparatus with the closed air supply circuit or in a closed-circuit breathing system rescue operations apparatus with the closed air supply circuit;

the device further comprises at least one functional component; and a heat-conducting element; and sending heat removed from the air by the at least one heat exchanger via the heat-conducting element to the at least one functional component, which is arranged within the closed air supply circuit.

12. A method in accordance with claim 11, wherein the at least one heat exchanger is arranged within the reaction zone.

13. A method in accordance with claim 11, wherein the at least one heat exchanger is configured with a plate-shaped heat-conducting element.

14. A method in accordance with claim 11, wherein the at least one heat exchanger has, in at least some sections, plastic-containing heat insulation on an outer surface thereof.

15. A method in accordance with claim 11, wherein the at least one heat exchanger has at least one heat-conducting lug extending into the reaction zone.

16. A method in accordance with claim 11, further comprising cooling the at least one heat exchanger with ambient air.

17. A method in accordance with claim 11, wherein the at least one functional component is configured as a flow sensor or as a pressure sensor or as both a flow sensor and as a pressure sensor.

18. A method in accordance with claim 11, wherein the device further comprises at least one material, which binds water, arranged in the condensate collection tank.

19. A method in accordance with claim 11, further comprising adding oxygen or an anesthetic gas to the air during the processing or adding both oxygen and an anesthetic gas to the air during the processing.

20. A device for a closed air supply circuit, the device comprising:

a housing;

carbon dioxide absorbing material arranged in said housing, said carbon dioxide absorbing material being configured to absorb carbon dioxide, and to generate heat and water when absorbing carbon dioxide;

a condensate collection tank arranged in said housing under said carbon dioxide absorbing material, said condensate collection tank being configured to collect water generated from the carbon dioxide absorbing material absorbing carbon dioxide;

a heat exchanger arranged in said housing, and configured to remove heat generated from the carbon dioxide absorber material absorbing carbon dioxide, said heat exchanger being configured to transfer heat from the carbon dioxide absorbing material to another device in contact with breathing air in the closed air supply circuit to prevent condensation in the another device.

21. A device in accordance with claim 20, wherein:

said carbon dioxide absorbing material is formed as a cartridge;

said housing is configured to remove said cartridge and said condensate collection tank from the closed air supply circuit at the same time.

22. A device in accordance with claim 20, wherein:

said carbon dioxide absorbing material and said condensate collection tank are configured to have said tank hold all water generate-able from said carbon dioxide absorbing material absorbing the carbon dioxide.

23. A device for a closed air supply circuit, the device comprising:

a housing;

carbon dioxide absorbing material arranged in said housing, said carbon dioxide absorbing material being configured to absorb carbon dioxide, and to generate heat and water when absorbing carbon dioxide, said carbon dioxide absorbing material being a cartridge;

said housing is configured to remove said cartridge and a condensate collection tank from the closed air supply circuit at the same time;

said condensate collection tank arranged in said housing under said carbon dioxide absorbing material, said condensate collection tank being configured to collect water generated from the carbon dioxide absorbing material absorbing carbon dioxide;

a heat exchanger arranged in said housing, and configured to remove heat generated from the carbon dioxide absorber material absorbing carbon dioxide.

* * * * *